United States Patent [19]

Abramowitz

[11] 4,294,356
[45] Oct. 13, 1981

[54] DENTAL MIRROR PROTECTOR CASE

[76] Inventor: Herbert Abramowitz, 143-19 25th Ave., Whitestone, N.Y. 11357

[21] Appl. No.: 141,994

[22] Filed: Apr. 21, 1980

[51] Int. Cl.³ .................. A45C 11/00; B65D 85/38
[52] U.S. Cl. ............................. 206/368; 206/316; 433/31; 433/30; 150/52 R; 128/21; 350/308
[58] Field of Search .......... 206/368, 349, 362.3, 206/0.82, 5.1; 433/31; 350/308, 305; 128/21; 150/52 R

[56] References Cited

U.S. PATENT DOCUMENTS

| | | | |
|---|---|---|---|
| 548,817 | 10/1895 | Platt | 433/31 |
| 2,372,280 | 3/1945 | Johnston | 150/52 R |
| 2,388,221 | 10/1945 | Smith | 206/0.82 |
| 2,947,412 | 8/1960 | Tupper | 206/362.3 |
| 3,339,608 | 9/1967 | Brenner | 150/52 R |
| 4,244,466 | 1/1981 | Arnhem | 206/5.1 |

*Primary Examiner*—William T. Dixson, Jr.

[57] ABSTRACT

In a preferred embodiment of the invention, a mirror antiscratch protector case mountable on a dental mirror, having a spaced-away recess portion of an interior concave wall surface with spaced-apart points on the interior concave wall surface on each of opposite sides of the recess portion supportable of mirror bezel structure of mirror mounting structure, and having a biasing spring positioned to press a mounted dental mirror's mirror bezel structure against the spaced-apart points, and having a barrier structure pressing against a leading edge of the mirror bezel structure when the mirror is mounted within the protector case such that the reflective surface of the mounted mirror is retained opposite the recess portion, with opposite edges of the protector case in alignment with the spaced-apart points converging from a wide to narrow width of the protector case such that varying sizes of dental mirrors are received and such that narrower portions of the concave wall surface serve as the barrier structure.

12 Claims, 9 Drawing Figures

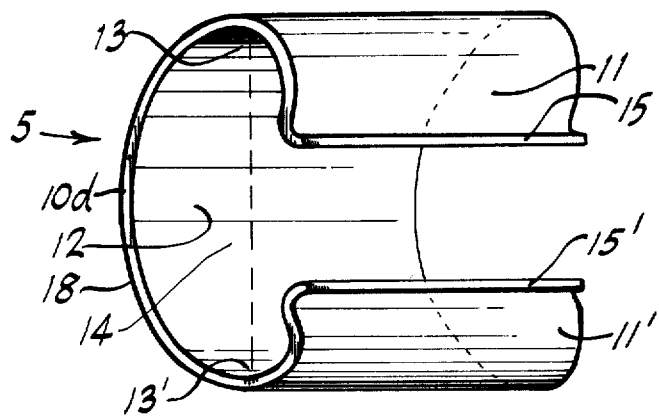
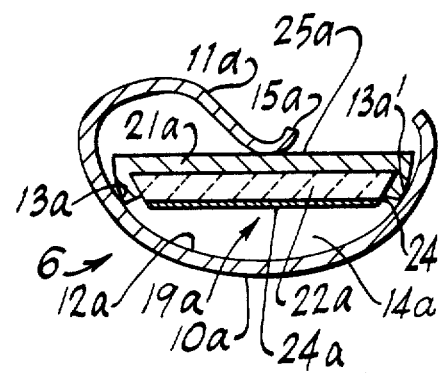
FIG. 1A
FIG. 1AA
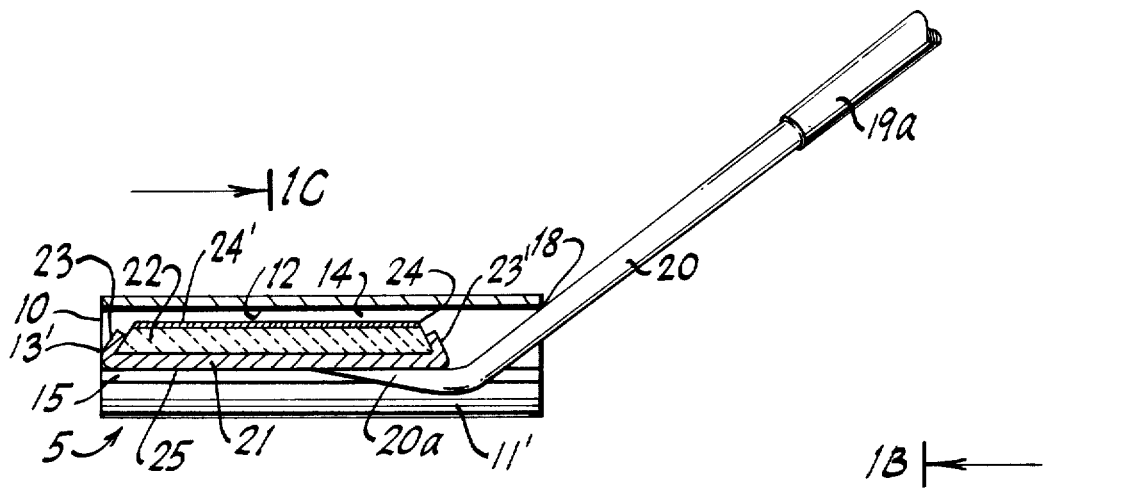
FIG. 1B
FIG. 1C
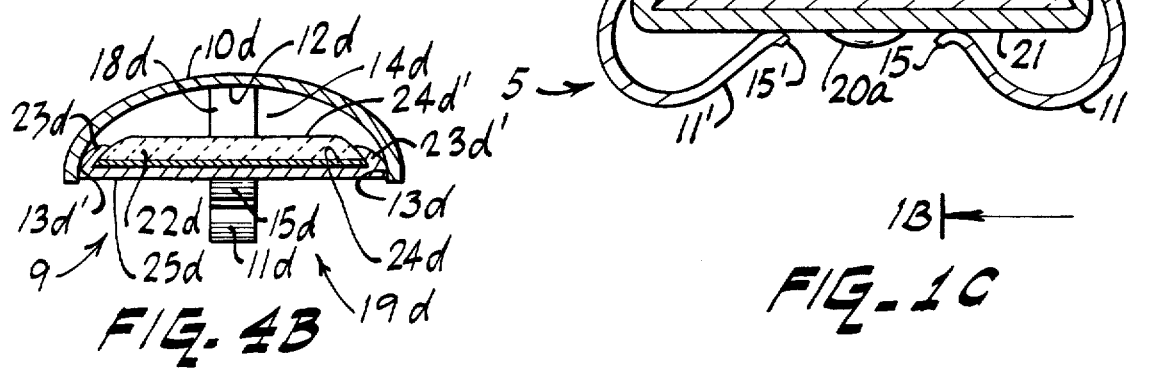
FIG. 4B

DENTAL MIRROR PROTECTOR CASE

This invention relates to a novel protector case for dental mirror reflective surfaces for use during sterilization.

BACKGROUND TO THE INVENTION

Prior to this invention, particularly in the field of dentistry where the dental mirror is an important instrument and requires unimpaired reflective surfaces, and also where such dental mirrors are very costly especially for the high quality front-coated mirrors, a major problem of scratching of the reflective surface has existed as incurred during sterilization and storage periods. Typical sterilization methods include dry heat in an oven at about 450 degrees Fahrenheit, and moist heat in an autoclave at about 253 degrees Fahrenheit, and cold sterilization in for example a solution of zephiran chloride or the like, and dry gas sterilization by poisonous gas such as ethylene oxide. In any one or more of these procedures of sterilization, dental instruments are generally placed into a tray or other container together, and it is the other instruments that accidentally strike and scar or scratch the dental mirror's reflective surface. While normally no one scratch is severe enough to fully thwart further use of the dental mirror, repeated scratches during the frequent and repeated sterilizations soon make use of mirror difficult, and eventually too poor for further use.

Heretofore there has been no available protective case or other practical way of protecting such dental mirrors that in normal procedures must be frequently sterilized as above-noted. A conventional cover or casing could itself touch and scratch the mirror surface. Also such casing, if any would have to be able to withstand the various conditions above-noted during such sterilizations. Any such case or protector would have little utility if it could not be utilized with conventional dental mirrors and without interfering with the normal utility of such dental mirrors; that is to say that such case or protector can not be a part integrally of the mirror, because as such the dental mirror could no longer be used for unimpaired movement within the limited spaces of the mouth. Likewise, such casing cannot be bulky and cumbersome, and should be easily but sturdily mountable and dismountable from the dental mirror.

U.S. Pat. No. 1,540,409 discloses solely a double vision mirror that can be opened and closed on the interconnecting hinge mounting one on the other. There is no mechanism for detaching one from the other and one is not intended to function without the other. The U.S. Pat. No. 2,434,311 discloses a semicircular member utilized to facilitate the moving of a filing into place within the mouth of a patient. While such do not relate to problems to which the present invention is directed, these patents represent the sole patents found in a novelty search.

BROAD DESCRIPTION OF THE INVENTION

Accordingly, objects of the present invention include the obtaining of a mirror protector for a dental mirror that overcomes the problems and meets the needs noted above.

In particular, an object of the invention is to obtain a dental mirror protector that is detachably mountable over the reflective surface to an extent that scratches thereon are avoided.

Another object is for such protector to be simply and quickly mountable and detachable.

Another object is for the protector to be small and of simple design and construction and low cost in manufacture.

Another object is for the protector to be of a nature that it can withstand a variety of various sterilization methods to which a dental mirror is normally subjected.

Another object is for the protector to be of a design and shape readily utilizable on currently available conventional dental mirrors.

Another object is to obtain a protector that fits securely on a dental mirror.

Another object is to obtain a protector that does not accidentally permit the mirror to be exposed by pushing the mirror beyond a protection position.

Another object is to obtain a protector that is of a design and shape adapted to be utilized equally well with diverse sizes and shapes of dental mirrors.

Other objects become apparent from the preceding and following disclosure.

One or more objects of the invention are obtained by the embodiments illustrated herein, in the accompanying drawings which are not intended to unduly limit the scope of the invention but are intended to merely improve understanding of the nature and preferred embodiments of the invention.

Broadly the invention may be defined as a mirror protector case that has a mirror cover mechanism including a cover structure having an interior concave surface of particular shape, together with an integral biasing spring that secures the cover structure onto a dental mirror, or other mirror as the case may be. The concavely shaped surface includes a recess spaced between two spaced-apart pressure points against which bezel structure of a dental mirror, for example, is pressed by the spring when the mirror is in the inserted state. The pressure points, for purposes of identification herein, are termed mirror-contact surfaces. The recess is sufficiently concave that exposed mirror reflective surface is devoid of contact with and is spaced from the interior surface when the mirror bezel structure is pressed against the spaced-apart mirror-contact surfaces.

In one preferred embodiment, there is included a barrier structure which serves to prevent the mirror from being accidentally pushed too far through the space in which protection is afforded to the mirror surface. That is to say, if the mirror is pushed past and beyond the protective space, it would otherwise then be again subjected to the hazards of scratching.

In the various embodiments, the cover structure is shaped in such an arcuate shape as to avoid lateral slipping of the dental mirror.

In another preferred embodiment, the cover structure is shaped to form an interior converging channel adapted to accept any of many diverse mirror diameters.

In another preferred embodiment, the cover structure is substantially semicircular along an axis that extends between the spaced-apart mirror-contact surfaces.

In another preferred embodiment, the spring structures is composed of an extension of the barrier structure.

In still another preferred embodiment, the spring structure is an arcuate flange extension of and from at least one edge of the cover structure, more preferably one from each of opposite edges in opposing relationship.

The invention may be better understood by reference to the following Figures.

THE FIGURES

FIG. 1A illustrates a dental mirror protector in a bottom perspective view.

FIG. 1B further illustrates the embodiment of FIG. 1A, showing the mirror protector mounted on a dental mirror, illustrated in a side cross-sectional view, as taken along lines 1B—1B of FIG. 1C.

FIG. 1C illustrates a different cross-sectional view of the mirror protector mounted on the dental mirror, as taken along lines 1C—1C of FIG. 1B.

FIG. 1AA illustrates a side cross-sectional view of a different other embodiment of the invention, showing this mirror protector mounted on a dental mirror, the mirror being also shown in cross-section.

Figure 3A:
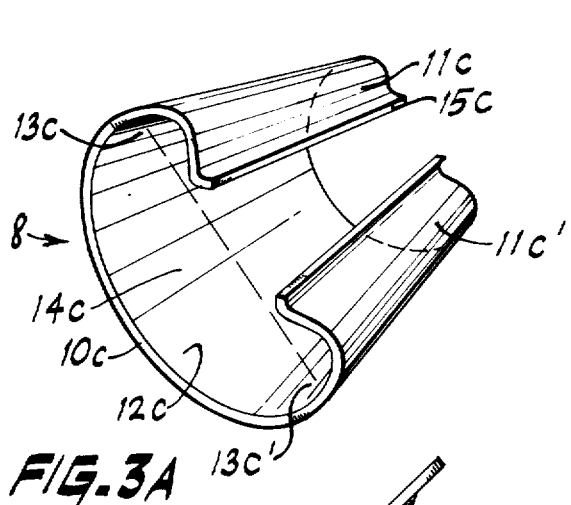
FIG. 3A illustrates still another preferred embodiment of the dental mirror protector of the invention, illustrated in a bottom perspective view.
Figure 3B:
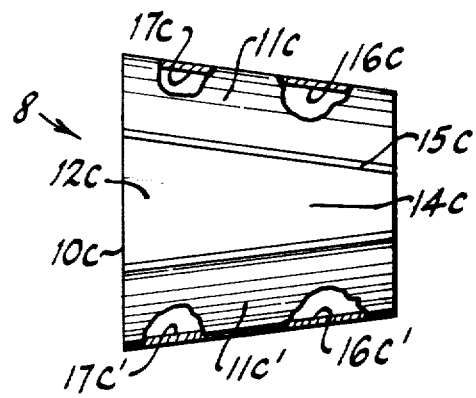

FIG. 3B further illustrates the FIG. 3A embodiment, shown here in a bottom elevation plan view.

Figure 4A:
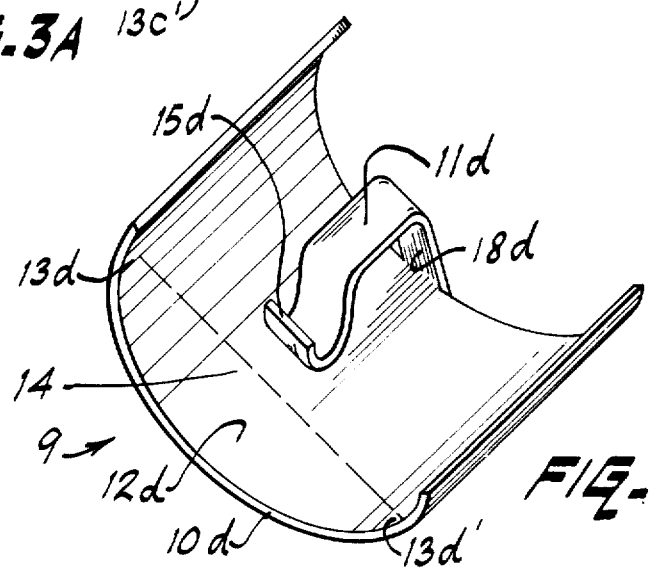

FIG. 4A illustrates an alternate preferred embodiment of a dental mirror protector, shown in a bottom perspective view.

FIG. 4B further illustrates the embodiment of FIG. 4A in a state of having a dental mirror mounted therein, the mirror and protector being both shown in a perspective side view.

DETAILED DESCRIPTION OF THE INVENTION

Figure 2:
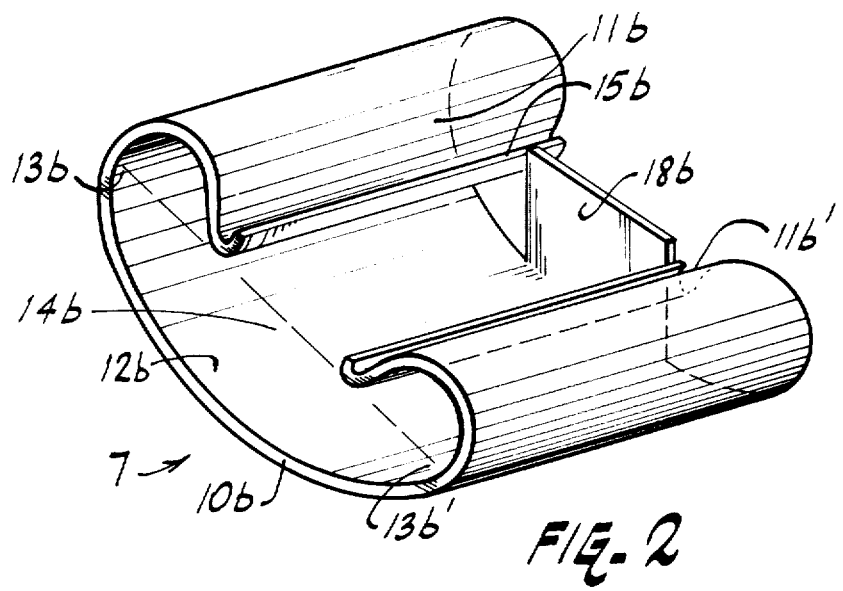
FIG. 2 illustrates a different embodiment as a variation on that of FIG. 1A, also a dental mirror protector in a bottom perspective view.

In greater detail, it is noted that FIGS. 1A, 1B, and 1C all disclose a common embodiment of the invention. The FIG. 1A is a variation and different embodiment basically the same in operation and operative design as that of the FIG. 1A embodiment. FIG. 2 differs from the FIG. 1A embodiment only in that the FIG. 2 embodiment includes a barrier structure previously described. The FIGS. 3A, 3B and 3C embodiment also is basically the same in design and operation as that of FIG. 1A except that the FIG. 3A embodiment is of a converging shape with a resulting utility equivalent to the FIG. 2 barrier structure embodiment, both serving to prevent excessive insertion of a mirror beyond an area or location at which the mirror would receive protection for its reflective surface. Additionally, however, the FIGS. 3A, 3B, and 3C embodiment is better adapted and directed toward the utility to receive a variety of diverse sizes of dental mirrors all equally well. On the other hand, a substantial difference in design is represented in FIGS. 4A and 4B embodiment, in that the barrier and spring are a combined structure and that the spring is not an extension as flanges from the side portion(s) but is a barrier extension from the end-located barrier structure. There is a common similarity of basic design of the cover structure, the differences being in the nature of the spring(s) location(s) and the nature of a barrier and its design.

With this general comment for improved understanding of the common invention embodied in all embodiments, we turn now to the description of the individual elements of the various embodiments, for improved following and understanding, using common indicia for common elements of the different embodiments, except for the different embodiments having different accompanying letters be associated with that embodiment. Accordingly, description shall not be repeated for common elements, such being redundant, and solely the different or additional features being pointed out.

Accordingly, FIGS. 1A, 1B and 1C disclose the mirror protector 5 of semicircular configuration having inner concave surfaces inclusive of the recess point 12 located between contact points or mirror pressure points 13d and 13d' and forming the mirror-receiving space 14 formed by the semicircular shape of the cover structure 10. Arcuate flanges 11 and 11' are spring structures as continuations of and extensions from opposite edges of the semicircular cover structure 10, each of the arcuate flanges having turned-up ends 15 and 15' facilitating the sliding of a mirror under the spring-like ends of the arcuate flanges and simultaneously avoiding scarring or scratching the backside of the mirror mount structure of the dental mirror. The FIGS. 1B and 1C illustrate the state of a dental mirror 19 having handle shaft 20 and handle 19, mirror-inserted within the mirror protector; the mirror portion includes the mirror mount structure 21 mounted on the shaft end 20a, with the bevel structures 23 and 23' securing the mirror 22 that has a front surface coating 24 with reflective surface 24' within the free-space 14 spaced from the recess point 12. The bevel structures (annular) at left and right are pressed-against the mirror pressure points 13 and 13'. In this embodiment, the cover structure 10 has a forward edge 18 against which the angled mirror handle shaft 20 abuts thus preventing the mirror 22 from being inserted too far beyond the protection of the cover structure 10.

In the embodiment of FIG. 1A, there is the mirror protector 6 having merely a single arcuate flange as a single spring, illustrated in a mounted state on a mirror having a front surface coating 24.

FIG. 2 is illustrative of a mirror protector case 7 basically similar to the structure of FIG. 1A except additionally inclusive of the barrier structure 18b that abuts a forward edge of the bevel structure of a dental mirror when it is fully inserted, preventing the possibility of too great an insertion to possibly expose a mirror reflective surface to scratching.

FIGS. 3A and 3B differ from the embodiment of FIG. 1A in the converging shape of inner surfaces 17c and 17c' shown best in FIG. 3B, showing the forward-wedge abutting points 16c and 16c' viewable in the cutaway portions, for this embodiment of mirror protector case 8.

FIGS. 4A and 4B illustrate the mirror protector case 9 devoid of arcuate flanges but having the barrier structure 18d extended as the spring 11d having upturned spring end 15d. Again as above-described for prior embodiments, the FIG. 4B illustrates the bevel edges 23d and 23d' pressed by the spring 11d against contact points 13d and 13d', for the back-surface coated mirror 22d having backcoating 24d, for the mirror exposed surface 24d'.

Normally the mirror portion 22, and 22d, are of glass and the coatings such as front-surface coating 24 and backsurface coating 24d are silver coating. Any conventional or desired coating support may, however, be utilized for front-surface coated mirrors; for example recently heat resistant plastic has been utilized. In like manner, the particular composition of the mirror cover structure and as well the spring structure may be of any appropriate structure such as metal or thermoplastic or the like.

In the utilization of the mirror protector case of the invention, it is thus merely necessary to slip the mirror forwardly into the space such as 14, or 14a, or 14b, or 14c, or 14d with the reflective surface facing the recess point such as 12 or 12a or 12b or 12c or 12d with the spring such as 11 or 11a or 11b or 11c or 11d pressing against a rearward surface of the mirror mount structure 21 for example.

It is within the scope of the invention to make such variations and modifications and substitution of equivalents as would be apparent to a person having ordinary skill in this field, noting however that the present invention is not limited to dental mirrors but may be equally well applied to other mirrors. However, the primary utility and problems to which the invention is directed is in the field of dentistry, although such similar type mirrors are utilized in other fields such as mechanics, for example.

I claim:

1. A mirror protector case comprising in combination: a mirror cover means for protecting a mirror reflective surface against contact with exterior objects and against contact with an interior surface of the mirror cover means, said mirror cover means including a cover structure having an interior-space surface of concave shape formed as a centrally positioned recess positioned between spaced-apart mirror-contact surfaces, and said mirror cover means further including spring structure mounted on said cover structure and positioned to exert biasing pressure against a rearward wall of a mirror such that mirror bezel structure on each of opposite sides of and adjacent to reflective mirror structure, is pressed against said spaced-apart mirror-contact surfaces, said recess being sufficiently concave that exposed mirror reflective surface is devoid of contact with and is spaced from said interior surface when mirror bezel structure is pressed against the spaced-apart mirror-contact surfaces.

2. A mirror protector case of claim 1, in which said mirror cover means includes barrier structure positioned such that when a mirror is mounted between said spring structure and said spaced-apart mirror-contact surfaces, said barrier structure presses against mirror bezel structure preventing further lateral movement of the mirror.

3. A mirror protector case of claim 2, in which said cover structure is substantially semicircular along an axis extending between said spaced-apart mirror-contact surfaces.

4. A mirror protector case of claim 3, in which said spring structure includes an arcuate flange extending from at least one edge of said cover structure.

5. A mirror protector case of claim 4, in which said spring structure is an extension of and continuation of said barrier structure.

6. A mirror protector case of claim 2, in which said spring structure includes an arcuate flange extending from at least one edge of said cover structure.

7. A mirror protector case of claim 6, in which said spring structure includes one of said arcuate flanges at each of opposite spaced-apart edges of said cover structure substantially in alignment with an axis extending between said spaced-apart mirror-contact surfaces.

8. A mirror protector case of claim 7, in which relative to a first axis extending between said spaced-apart mirror-contact surfaces, the cover structure extends along a second axis that is substantially perpendicular to said first axis and width of the cover structure as it extends along said second axis is wider at a first end of said second axis and narrowing to a narrower width at a second opposite end of said second axis, said narrower width being of a predetermined dimension of lesser width than a mirror to be mounted within said mirror cover means such that the cover structure at said narrower width functions as barrier structure that presses against a mirror bezel structure when a mirror is mounted within the mirror cover means.

9. A mirror protector case of claim 1, in which relative to a first axis extending between said spaced-apart mirror-contact surfaces, the cover structure extends along a second axis that is substantially perpendicular to said first axis and width of the cover structure as it extends along said second axis is wider at a first end of said second axis and narrowing to a narrower width at a second opposite end of said second axis, said narrower width being of a predetermined dimension of lesser width than a mirror to be mounted within said mirror cover means such that the cover structure at said narrower width functions as barrier structure that presses against a mirror bezel structure when a mirror is mounted within the mirror cover means.

10. A mirror protector case of claim 9, in which said cover structure is substantially semicircular along said first axis.

11. A mirror protector case of claim 10, in which said spring structure includes an arcuate flange extending from at least one edge of said cover structure.

12. A mirror protector case of claim 11, in which said spring structure includes one of said arcuate flanges at each of opposite spaced-apart edges of said cover structure substantially in alignment with said first axis.

* * * * *